United States Patent
Allen

(10) Patent No.: US 9,044,309 B2
(45) Date of Patent: Jun. 2, 2015

(54) ADJUSTABLE PELVIC COMPRESSION BELT AND METHODS FOR REDUCING THE WIDTH OF A USER'S HIPS

(75) Inventor: Janiene Allen, Austin, TX (US)

(73) Assignee: Shrinkx, Inc., Austin, TX (US)

( * ) Notice: Subject to any disclaimer, the term of this patent is extended or adjusted under 35 U.S.C. 154(b) by 937 days.

(21) Appl. No.: 12/719,568

(22) Filed: Mar. 8, 2010

(65) Prior Publication Data

US 2010/0234780 A1    Sep. 16, 2010

Related U.S. Application Data

(60) Provisional application No. 61/158,879, filed on Mar. 10, 2009.

(51) Int. Cl.
A61F 5/00 (2006.01)
A61F 5/02 (2006.01)
A61F 5/01 (2006.01)

(52) U.S. Cl.
CPC .............. *A61F 5/028* (2013.01); *A61F 5/0193* (2013.01)

(58) Field of Classification Search
CPC .......... A61F 5/028; A61F 5/0193; A61F 5/03
USPC ........................... 602/19, 2, 5; 128/96.1, 876, 128/99.1–101.1; D24/190
See application file for complete search history.

(56) References Cited

U.S. PATENT DOCUMENTS

| | | | | |
|---|---|---|---|---|
| 2,345,760 | A * | 4/1944 | Lunney | 450/113 |
| 3,783,879 | A * | 1/1974 | Stalder | 450/146 |
| 5,086,759 | A | 2/1992 | Buddingh | |
| 5,315,740 | A | 5/1994 | Provost | 24/452 |
| 5,407,422 | A * | 4/1995 | Matthijs et al. | 602/19 |
| 6,066,109 | A * | 5/2000 | Buser et al. | 602/23 |
| 7,037,284 | B2 | 5/2006 | Lee | |
| 7,160,262 | B2 | 1/2007 | Wicks | |
| 7,704,121 | B2 * | 4/2010 | Goodman | 450/155 |
| 7,882,574 | B2 * | 2/2011 | Arsenault et al. | 2/227 |
| D648,440 | S * | 11/2011 | Allen | D24/190 |
| 2006/0052304 | A1 | 3/2006 | Stewart | |
| 2007/0232973 | A1 | 10/2007 | Serola | |
| 2009/0142988 | A1* | 6/2009 | Goodman | 450/155 |

OTHER PUBLICATIONS

SlimmerTM Post-Pregnancy hip-slimming corset, Jun. 2008. http://hipslimmer.com.*
May 4, 2010 International Search Report and Written Opinion for related international application PCT/US10/26677.
Author Unknown, "Welcome to HipSlimmerTM," *SlimmerTM Post-Pregnancy hip-slimming corset.* Apr. 22, 2008. Date accessed Aug. 7, 2013. < http://hipslimmer.com>.
Author Unknown, "Questions?" *SlimmerTM Post-Pregnancy hip-slimming corset.* Jun. 9, 2008. Date accessed Aug. 6, 2013. < http://hipslimmer.com>.

* cited by examiner

*Primary Examiner* — Kim M Lewis
(74) *Attorney, Agent, or Firm* — Kilpatrick Townsend & Stockton LLP

(57) ABSTRACT

An adjustable pelvic compression belt for the reducing the width of, and/or realigning, a user's hips that is particularly adapted for post-parturition use. The belt may include an inner belt to be wrapped around the user's hips and positioned below the iliac crest. The midpoint of an outer belt may be attached to the inner belt at or near the midpoint of the inner belt. The ends of the outer belt may be adjusted to cinch the inner belt around the hips of the user, thereby compressing the user's pelvic girdle. Thereafter, the outer belt may be incrementally adjusted to further compress the user's pelvic girdle resulting in a narrowing of the user's hips. The belt is preferably worn within two to three months post-parturition or during a period in which relaxin is being administered to the user, and has a strength and thickness that facilitates use under garments.

5 Claims, 5 Drawing Sheets

ADJUSTABLE PELVIC COMPRESSION BELT AND METHODS FOR REDUCING THE WIDTH OF A USER'S HIPS

PRIORITY STATEMENT UNDER 35 U.S.C. §119 & 37 C.F.R. §1.78

This non-provisional application claims priority based upon prior U.S. Provisional Patent Application Ser. No. 61/158,879 filed Mar. 10, 2009 in the name of Janiene Allen entitled "Adjustable Pelvic Compression Belt/Wrap for reducing the hip measurement of post natal women," the disclosure of which is incorporated herein in its entirety by reference.

BACKGROUND OF THE INVENTION

The pelvic girdle, and in particular the pubic symphysis, undergoes a number of hormonally-facilitated structural modifications during pregnancy. More specifically, an increase in the amount of the hormone relaxin prior to delivery causes a laxity of the fibrocartilidge in the pubic symphysis, resulting in a gap between the hip bones on either side of the pubic symphysis, which facilitates the passage of the child through the birth canal. After parturition, the relaxin remains in the system for a period of time, thereby causing the pubic symphysis to retain, at least in part, its laxity. As relaxin leaves the system, it is not uncommon for gap between the hip bones after parturition to be greater than the gap between the hip bones before parturition. This widening of the hips is deemed undesirable by many. In some cases, misalignment of the pelvis may also result from, for example, a period of elevated relaxin and other causes. Misalignment of the pelvis can result in pain and other symptoms.

Some girdles and support belts have previously been developed, but none of these has been specifically intended to address the widening of the hips after parturition. Accordingly, the previously known devices suffer from drawbacks and disadvantages that make them unsuitable for use in addressing the widening of the hips, particularly after pregnancy.

For example, U.S. Pat. No. 7,037,284 to Lee describes an orthopedic pelvic compression belt for stabilization of specific aspects of the pelvic girdle. Lee's belt can be utilized in the strengthening rehabilitation of muscles in patients with muscle dysfunction in the deep abdominals, the deep back muscles, and the pelvic floor muscles. In accordance with its intended use designed for pelvic stabilization, Lee's main belt is made of an inelastic material, and also includes independent side straps for providing differing compression at different parts of the belt. These features make it undesirable for use in post parturition applications.

Pending U.S. patent application Ser. No. 11/278,632 of Serola describes a sacroiliac belt used to stabilize and reduce strain in the sacroiliac joint. The main member of Serola's belt also made of an inelastic material, and is made of a foam and fabric composite of substantial thickness. These features also make Serola's device unsuitable for use in post parturition applications. Moreover, there is no suggestion of using the Serola device in a position below the iliac crest of a user.

SUMMARY OF THE INVENTION

The invention provides methods and devices for reducing the post-parturition hip dimension, and/or realigning a user's hips, and may be implemented in a number of ways.

According to one embodiment of the invention, a device for reducing the width of, and/or realigning, a user's hips includes an inner belt having a first connector at a first portion of the inner belt and a second connector at a second portion of the inner belt, the first and second connectors being engageable to secure the inner belt around the user's hips at or below the iliac crest. In these embodiments, the device also includes an outer belt permanently affixed to the inner belt, and the inner surface of the outer belt has a third connector capable of being removably attached to the inner belt. When the inner belt is secured around the hips, the ends of the outer belt are adjustable to compress the inner belt around the hips and to connect the inner belt and the third connector to maintain compression. The inner belt may be elastic over a first portion of its length, and substantially inelastic over a second portion of its length, e.g., at its ends where hook and loop type fasteners may be located. Indeed, both the second and third connectors may be hook and loop fasteners. According to one particularly advantageous embodiment that facilitates use under garments, the width of the inner belt may be less than approximately 5 inches, and the thickness of the inner belt may be less than approximately 3 mm, e.g., 2 mm or less. The thickness of the outer belt may also be less than approximately 3 mm, e.g., 2 mm or less, and the thickness of the hook portion of the hook and loop fasteners may be less than approximately 1 mm, for example about 0.635 mm. A point at or near the midpoint of the outer belt may be affixed to a point at or near the midpoint of the inner belt. The second connector may span less than the entire outer surface of the inner belt. In some embodiments, the ends of the outer belt are not permanently attached to the inner belt, but are able to be removably attached to the inner belt, for example using third connectors provided at both ends of the outer belt.

According to another aspect of the invention, a method for reducing the width of, and/or realigning, a user's hips includes, securing a belt around the hips of the user during a time that is within 3 months after the user's giving birth to offspring. Compression may be applied through use of the belt to the user's hips. The belt may have first and second portions disposed around the hips and may be at or below the iliac crest of the user. The compression of the belt may then be adjusted by manipulating the second portion of the belt relative to the first portion and thereafter removably attaching the first and second portions together to maintain tension between the first and second portions. In certain embodiments, the belt may be secured around the hips of the user during a time when relaxin is administered to the user. The adjusting step may be repeated to incrementally increase the compression over time. The first portion may be an inner belt having a first connector at one end and a second connector positioned along the outer surface of the inner belt, and the second portion may be an outer belt, and the step of securing the belt around the user's hips may include positioning the inner belt around the user's hips and engaging the first and second connectors, which may be portions of a hook and loop fastener. The step of positioning the inner belt around the user's hips may include stretching an elastic portion of the inner belt, the belt being elastic over a first portion of its length and substantially inelastic over a second portion of its length. The outer belt may include at least one third connector, and the step of adjusting the compression of the belt may include removably attaching the third connector to the second connector. At least one article of clothing may be placed over the belt. so that the belt may be unobtrusively worn under clothing.

Additional features and advantages of the invention will be described hereinafter which form the subject of the claims of the invention. It should be appreciated by those skilled in the art that the conception and specific embodiment disclosed may be readily utilized as a basis for modifying or designing other structures or processes for carrying out the same purposes of the present invention. It should also be realized by those skilled in the art that such equivalent constructions do not depart from the spirit and scope of the invention as set forth in the appended claims.

DESCRIPTION OF THE DRAWINGS

For a more complete understanding of the present invention, and the advantages thereof, reference is now made to the following descriptions taken in conjunction with the accompanying drawings, in which.

DESCRIPTION OF THE PREFERRED EMBODIMENTS

Figure 1:
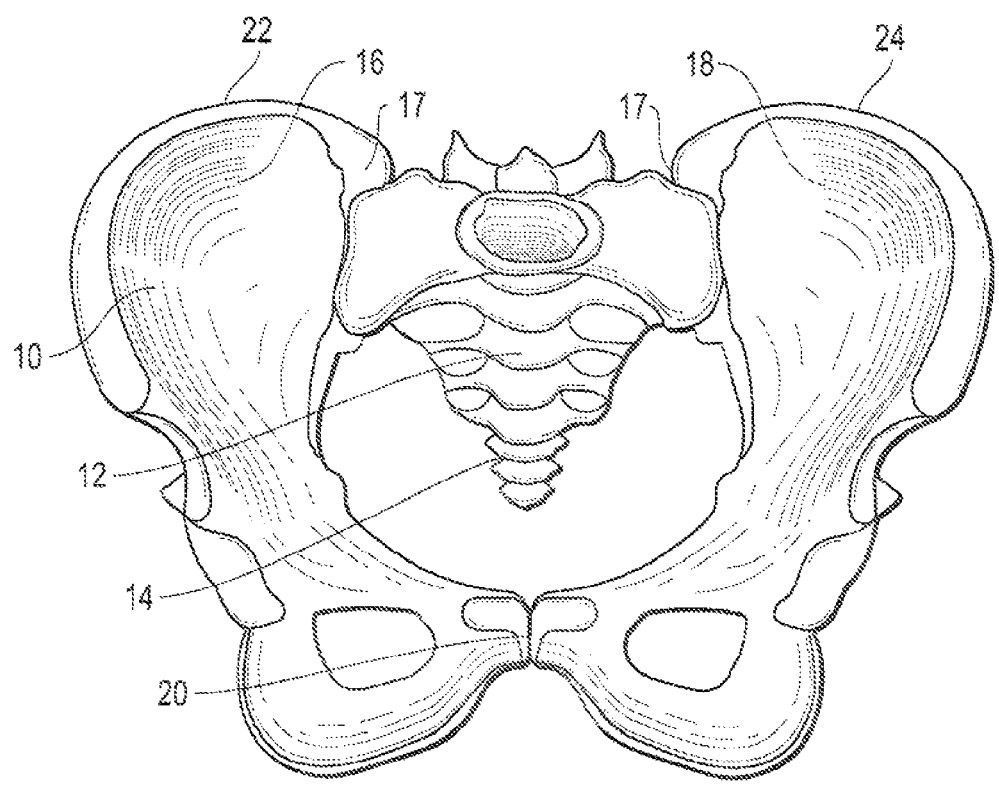
FIG. 1 is an illustration of the female pelvic girdle, including the sacrum, the coccyx, and the hip bones.

Embodiments of the invention are directed to improved methods and systems for narrowing, and/or realigning, hips post-pregnancy and, more specifically, to the application of a pelvic belt during the period in which the hormone relaxin is likely present in the body. The configuration and use of the presently preferred embodiments are discussed in detail below. It should be appreciated, however, that the invention provides many applicable inventive concepts that can be embodied in a wide variety of contexts other than post-pregnancy hip reduction and/or realignment. Accordingly, the specific embodiments discussed are merely illustrative of specific ways to make and use the invention, and do not limit the scope of the invention. In addition, references to hip reduction and other terms used herein may be applicable to periods other than during post-pregnancy such as, for example, during the administration of synthetic relaxin, and the like.

Embodiments of the invention provide an adjustable pelvic belt including an inner belt affixed to an outer belt. The pelvic belt may be positioned around the individual's hips within 2 to 3 months after parturition. The inner belt may be secured around the user's hips at or below the iliac crest and the outer belt used to cinch the inner belt tighter. Because the hormone relaxin is present in the individual's system during this period, the ligaments, joints, and connective tissue in the pelvic girdle remain pliable. The pressure exerted on the pelvic girdle by the adjustable pelvic belt helps force the right ilium and the left ilium to move together, thereby reducing the gap in the pubic symphysis. As the hormone relaxin is metabolized and is no longer present in large amounts, the ligaments, joints, and connective tissue in the pelvic girdle strengthen and stabilize and, because the stabilization occurs when the gap in the pubic symphysis is reduced, the hips are reduced to, or close to, pre-pregnancy width.

Collagens make up a large family of glycoproteins with at least 19 molecular forms, and are most abundant in the extracellular matrix of connective tissues. The mammalian reproductive tract is composed of a spectrum of collagen types including fibril-forming, fibrilassociated, basement membrane, microfibrillar and anchoring fibril collagens. The ability to regulate the amount and types of collagen in these connective tissues has a profound effect on tissue structure and function, which is crucial in growth and tissue repair processes such as those associated, with pregnancy and parturition. Even subtle alterations to collagen composition has dramatic implications with respect to the structural properties of the pelvic girdle and reproductive tract, whereby tissues may undergo conformational changes involving a turnover of specific collagen types to be able to accommodate delivery.

Relaxin is a polypeptide hormone with a similar structural identity to insulin. Relaxin affects collagen metabolism, inhibiting collagen synthesis and enhancing its breakdown by increasing matrix metalloproteinases. It is produced mainly by the corpus luteum, in both pregnant and non-pregnant females. It rises to a peak within approximately 14 days of ovulation and then declines in the absence of pregnancy resulting in menstruation. During the first trimester of pregnancy levels rise and additional relaxin is produced by the decidua. Relaxin's peak is reached during the 14 weeks of the first trimester and at delivery. Relaxin has a number of potential biological functions and has been shown to play a significant role in softening connective tissue in the pubic symphysis and cervix in preparation for birth of the fetus. After delivery, relaxin levels gradually dissipate for the next six to eight weeks and loosened pelvic joints and ligaments begin to tighten and stabilize.

Figure 2:
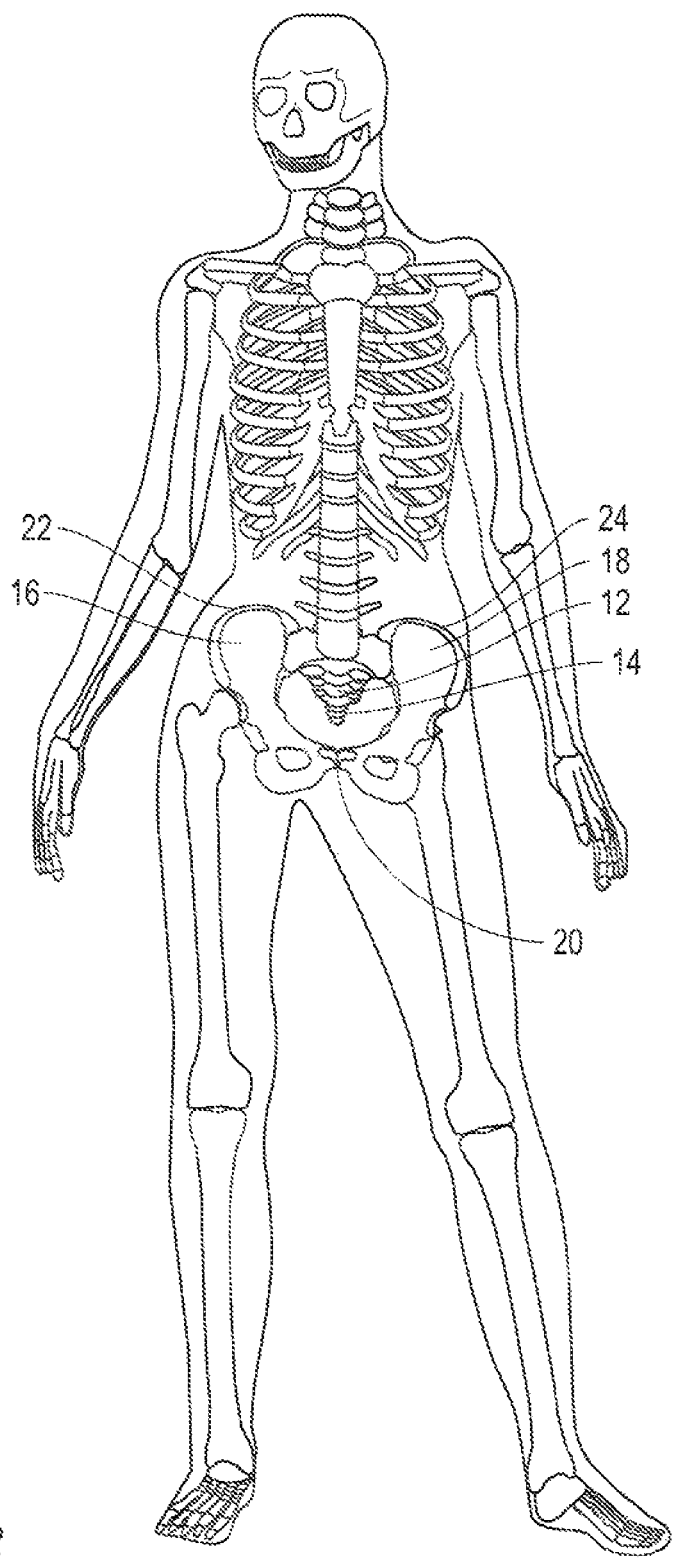
FIG. 2 is an illustration of a female skeleton including the pelvic girdle.

Referring now to FIG. 1 and FIG. 2 showing aspects of the female pelvic girdle 10, sometimes called the pelvic ring, the hip girdle or the coxa girdle, which connects the spine to the femurs. In the adult human, the pelvic girdle 10 is formed in the back by the sacrum 12 and the coccyx 14, and laterally and posteriorly by the right ilium 16 and the left ilium 18. At the top of the right ilium 16 is the right iliac crest 22 and at the top of the left ilium 18 is the left iliac crest 24. The right ilium 16 and the left ilium 18 are connected to each other anteriorly at the pubic symphysis 20, and posteriorly to the sacrum 12 at the sacroiliac joints 17 and 19. Because the pelvic girdle 10 is instrumental in transmitting loads from the trunk to the lower limbs, it is generally very stable and has very little mobility.

The right ilium 16 and the left ilium 18 are joined at the pubic symphysis 20, a non-synovial amphiarthrodial joint. This joint is connected by fibrocartilage and may contain a fluid filled cavity with a center that is generally avascular. The ends of the right ilium 16 and the left ilium 18 are covered by a thin layer of hyaline cartilage which has a slimy mass with a firm consistency and considerable elasticity. The hyaline cartilage is attached to the fibrocartilage.

As might be expected, women have a greater thickness of the pubic symphysis which allows more mobility of the pelvic bones, hence providing a greater diameter of pelvic cavity during childbirth. In addition, during pregnancy, hormones such as relaxin allow the pelvic bones to be more flexible for delivery. The non-pregnant gap of the pubic symphysis is 4-5 mm but, in pregnancy, there will be an increase of at least 2-3 mm. Therefore, a total width of up to 9 mm between the two ilium bones is considered normal for a pregnant woman. This natural extra gapping due to relaxation of the pelvic articulations, including the pubic symphysis, decreases following the delivery, although the supporting ligaments will take three to five months to regain stability. In some women there can even be a diastasis of the pubic symphysis during delivery, particularly in the case of a rapid birth or a forceps delivery, in which case recovery could be considerably longer.

As previously described, the hormone relaxin assists with the softening of the connective tissue of the pelvic girdle and remains in the body for 6 to 8 weeks post parturition. Unless pressure is placed on the pelvic girdle pushing the right ilium 16 and the left ilium 18 together at the pubic symphysis, the fibrocartilage remains lax and the gap in the pubic symphysis remains. This gap in the pubic symphysis causes a woman's hips to the wider after parturition than before. This widening of the hips is considered undesirable by some and is frequently dismissed by healthcare professionals unless the laxity of the pelvic girdle results in pubic symphysis dysfunction. This process, and other causes, may also result in misalignment of the hips, and related components of the pelvic girdle, that can cause pain and other symptoms.

Figure 3:
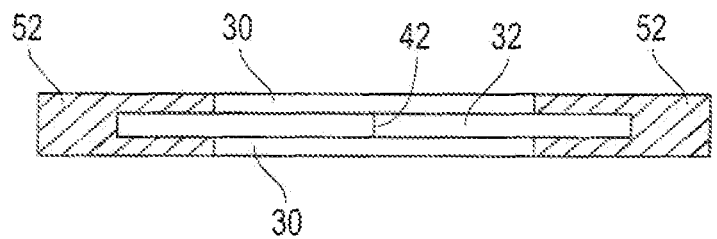
FIG. 3 is a top view of one embodiment of an adjustable pelvic belt constructed according to the principles of the invention.
Figure 4:
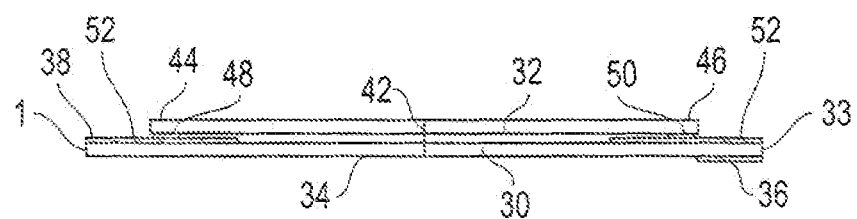
FIG. 4 is a side view of the adjustable pelvic belt of FIG. 3.

Referring now to FIG. 3 and FIG. 4, there is shown one embodiment of the pelvic compression belt of the invention. The belt may include two separate belt elements: an inner belt 30 and an outer belt 32. In one embodiment, the inner belt 30 is made of an elastic material but may be made, in whole or in part, of any elastic or inelastic fabric or non-fabric material which is suitable for being removably secured around the user's hips. For example, inner belt 30 may include a lightweight, breathable, 4-way stretch knit fabric made of a blend of nylon and elastane surrounding a width of woven elastic. One commercial version of elastane is known under the trade name Spandex™. In some embodiments, the fabric may comprise about 80 percent nylon and about 20 percent elastane. The woven elastic may be latex free. The inner belt 30 is sized in length to wrap around a user's hips and to allow the two ends 31 and 33 of the inner belt 30 to connect. The inner belt 30 is sized in width to fit comfortably under the iliac crest, but preferably no wider than 5 inches. The ends of the inner belt 30 may be connected using hook and loop fasteners, buckles, zippers, snaps, adhesives, magnets, or by other methods known in the art.

In one embodiment, the inner surface 34 of inner belt 30 is affixed with the hook portion 36 of a hook and loop fastener so that, when inner belt 30 is placed around a user's hips, the hook portion 36 removably engages with the loop portion 38 of a hook and loop fastener to secure the inner belt 30 to the users hips.

The outer belt 32 can also be made, in whole or in part, of an elastic material but may be made of any fabric or non-fabric material. In some embodiments, inner belt 30 and outer belt 32 are made of identical materials, except for any attachment surfaces and fasteners. A midpoint between the two ends of the outer belt 32 is either permanently or removably affixed at or near the midpoint between the two ends 31 and 33 of the inner belt 30, using a connector, fastener, adhesive, stitching, or other suitable means 42 known in the art. The ends 44 and 46 of the outer belt 32 are configured with connectors 48 and 50 to removably secure the ends 44 and 46 of the outer belt 32 to the outside of inner belt 30. The outer belt 32 is sized in length so that the ends 44 and 46 of outer belt 32 are shorter than, and do not interfere with, the ends 31 and 33 of inner belt 30. The outer belt 32 is sized in width to be no wider than the widest part of the inner belt 30. Connectors 48 and 50 may be any means of removably affixing ends 44 and 46 of outer belt 32 to the outside of inner belt 30, including hook and loop fasteners, buckles, zippers, snaps, adhesives, magnets, or by other methods known in the art.

In one embodiment, inner belt 30 is configured with a loop material 52 along all or a portion of its outer surface. Connectors 48 and 50 on the inside of outer belt 32 consist of hook material and the hook material can be coupled directly to loop material 52 to secure the ends 48 and 50 to the inner belt 30. The hook material may be, for example, a low to extremely low profile, high density hook design that provides superior closure and shear strength. Molded hooks may be made of materials such as a nylon mixture to provide good cycling life with both low profile and non-woven loop materials.

In some embodiments, loop material 52 is not elastic, so that the portions of the length of inner belt 30 to which loop material 52 is affixed may not be elastic. Thus when loop material is provided over only a portion of the length of inner belt 30, inner belt 30 may be elastic over a first portion of its length, and substantially inelastic over a second portion of its length by virtue of the inelasticity of the loop material. One or more portions of the length of inner belt 30 may be rendered substantially inelastic in other ways as well, for example by making a portion of inner belt 30 from an inelastic material.

Belts in accordance with embodiments of the invention are not intended to cause immobility of the pelvis, as in the prior art, but instead give constant, even pressure to the pelvis. An at least partially elastic inner belt 30 allows the belt to stretch and flex with the user, enabling the user to comfortably wear the belt for as many hours as possible without interfering with normal daily activity. Also, using similar materials for at least parts of inner belt 30 and outer belt 32 assists in keeping the pressure consistent and even. Both inner belt 30 and outer belt 32 are able to move with the user for long term wear and comfort. Having outer belt 32 affixed to inner belt 30 facilitates easy adjustment of the tension in the belt and promotes even tension on both sides of the user, in contrast with a design in which multiple outer belt pieces are used.

Figure 5:
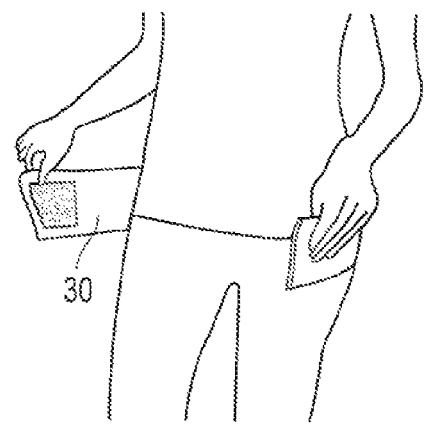
FIG. 5 is a perspective view of another embodiment of an adjustable pelvic belt of the invention being donned by a user.
Figure 6:
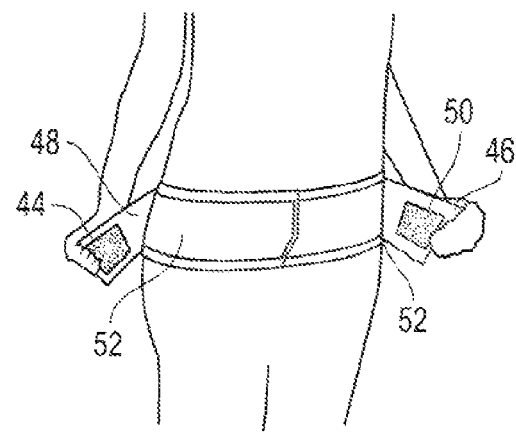
FIG. 6 is a perspective view of the adjustable pelvic belt of FIG. 5 being adjusted by a user.
Figure 7:
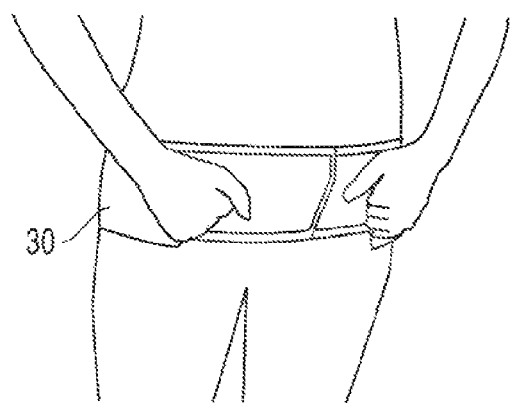
FIG. 7 is a perspective view of the adjustable pelvic belt of FIG. 6 being worn by a user.

FIG. 5, FIG. 6 and FIG. 7 show one embodiment of the use of a pelvic compression belt of the invention. Commencing as soon as comfortably possible post-parturition and continuing as long as desired by the user during the period in which relaxin is present in meaningfully-increased levels, the inner belt 30 may be wrapped around the users hip and positioned at or below the right and left iliac crests. In embodiments, the belt may be positioned below the iliac crest in order to provide additional stability and effectiveness. For example, such positioning may provide a more even pressure along a greater portion of the pelvic girdle in certain circumstances. Preferably, the inner belt 30 is placed snuggly around the hips so the belt is tightly secured to maximize the effect of adjustments to the outer belt 32. The ends 44 and 46 of the outer belt 32 are pulled forward to cinch inner belt 30 around the users hips and the connectors 48 and 50 on the inside of outer belt 32 are affixed to loop material 52 on the outside of inner belt 30. Because the midpoint of the outer belt 32 is secured to the inner belt 30 at or near the midpoint 42 of the inner belt 30, it is easily possible to apply steady even pressure when pulling the two ends of the outer belt 32.

Once the inner belt 30 has been secured around the user's hips and tightened by tensioning or tightening the ends 44 and 46 of the outer belt 32, the pressure will cause a narrowing of the pelvic girdle resulting in a reduction in the width of the user's hips. The pressure may also assist in realigning misaligned portions of the hips. Over time, the original tension applied by the outer belt 32 will be insufficient to cause further narrowing, at which time the ends 44 and 46 of the outer belt 32 may be adjusted through the application of additional pressure. This incremental tightening of the inner belt 30 through one or more adjustments of the outer belt 32 results in a further narrowing of the hips. This incremental adjustment may continue until the user achieves the desired results or until relaxin is no longer meaningfully present in the user's system.

As will be appreciated by those skilled in the art, the efficacy of the adjustable pelvic belt improves in proportion to the length of time over which the belt is worn each day. Accordingly, some users may prefer to wear the belt under their clothing, for example by placing and wearing an article of clothing over the belt. In one embodiment, the thickness of the inner belt 30 is between 1.0 mm and 3.0 mm, and preferably about 2.0 mm, and the thickness of the outer belt 32 is between 1.0 mm and 3.0 mm, and preferably about 2.0 mm. In combination, the inner belt 30 and the outer belt 32 are thin enough that they may be secured around the user's hips under the user's clothing. As a result, the user can wear the belt while engaging in their normal activities, thereby extending the likelihood that the belt will be worn for extended periods each day. To enable the thin profile of the belt, either or both of inner belt 30 and outer belt 32 preferably include a very thin fabric shell. Additionally, loop material 52 is preferably a lightweight low profile knitted loop, and hook portion 36 and connectors 48 and 50 are preferably made of a very low profile, molded hook material. For example, the hook material may have a thickness of less than approximately 1 mm, for example, about 0.635 mm. In some embodiments, neither inner belt 30 nor outer belt 32 includes any foam or other cushioning material that might add to the overall thickness of the belt. In contrast to designs having inelastic belts, the need for any additional cushioning is alleviated in part by the at least partially elastic nature of inner belt 30. This of course, facilitates its use as an undergarment, which may be highly desirable in post-parturition uses.

Figure 8:
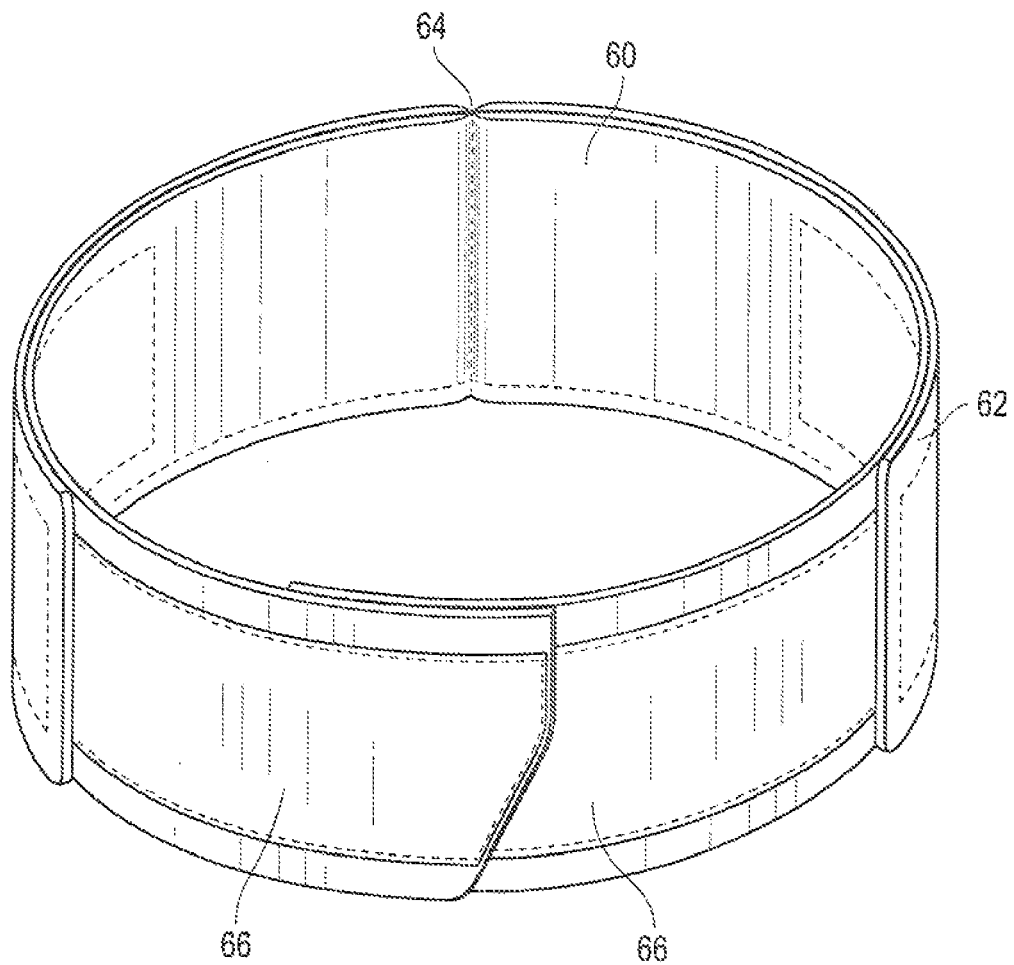
FIG. 8 is a perspective view of another embodiment of an adjustable pelvic belt constructed according to the principles of the invention.

FIG. 8 shows a perspective view of another embodiment of an adjustable pelvic belt constructed according to the principles of the invention. In this view, the belt is in a position as if it were secured to a user. In this embodiment, inner belt 60 and outer belt 62 are joined near the midpoints by means 64, which may be stitching, a fastener, and adhesive, or any other suitable means known in the art. Inner belt 60 and outer belt 62 are of substantially equal width, for example preferably 5 inches or less. Inner belt 60 comprises loop material 66 over a portion of the outer surface of inner belt 60, forming a first connector. A portion of the inner surface of inner belt 60 is preferably covered with a hook material for engaging with loop material 66 to secure the belt around the user. The ends of outer belt 62 also include patches of hook material to engage loop material 66. The compression on the hips of the user can thus be adjusted by repositioning the ends of outer belt 62 in relation to inner belt 60, as has been previously described.

While the adjustable pelvic belt has been described for most advantageous use during the two to three months post-parturition, those skilled in the art will recognize that, because efficacy of the belt is dependent on the laxity of the pelvic girdle, which may naturally be caused by the presence of the relaxin hormone after birth, it is possible to achieve the same effects through the use of the belt in conjunction with the simultaneous administration of human or synthetic relaxin, and the like. In such a case, hip reduction and/or realignment could also occur even in the absence of pregnancy, e.g., for cosmetic and/or therapeutic purposes.

While the above disclosure relates to the preferred embodiments of the invention, those of ordinary skill in the art will understand that other embodiments have also been enabled. Even though the foregoing discussion has focused on particular embodiments, it is understood that other configurations are contemplated. In particular, even though the expressions "in one embodiment" or "in another embodiment" are used herein, these phrases are meant to generally reference embodiment possibilities and are not intended to limit the invention to those particular embodiment configurations. These terms may reference the same or different embodiments, and unless indicated otherwise, are combinable into aggregate embodiments. The terms "a", "an" and "the" mean "one or more" unless expressly specified otherwise. The term "connected" means "communicatively connected" unless otherwise defined.

When a single embodiment is described herein, it will be readily apparent that more than one embodiment may be used in place of a single embodiment. Similarly, where more than one embodiment is described herein, it will be readily apparent that a single embodiment may be substituted for that one device.

In light of the wide variety of methods for reduction of hip width and realignment of the hips, the detailed embodiments are intended to be illustrative only and should not be taken as limiting the scope of the invention. Rather, what is claimed as the invention is all such modifications as may come within the spirit and scope of the following claims and equivalents thereto.

None of the description in this specification should be read as implying that any particular element, step or function is an essential element which must be included in the claim scope. The scope of the patented subject matter is defined only by the allowed claims and their equivalents. Unless explicitly recited, other aspects of the invention as described in this specification do not limit the scope of the claims.

What is claimed is:

1. A method for reducing the width of a user's hips, the method comprising the steps of:
    securing a belt around the hips of the user during a time when relaxin is present at elevated levels in the user's system due to recent pregnancy;
    applying compression through use of the belt to the user's hips to narrow the user's hips, wherein the applied compression is insufficient to cause immobility of the pelvis of the user; and
    adjusting the compression of the belt by manipulating a second portion of the belt relative to a first portion and thereafter removably attaching the first and second portions together to maintain tension therebetween, wherein the first portion is an inner belt having a first connector at one end and a second connector positioned along the outer surface of the inner belt, and wherein the second portion is an outer belt, and wherein said step of securing the belt around the hips of said user comprises positioning the inner belt around the hips of the user and engaging the first and second connectors.

2. The method of claim 1, further comprising repeating said adjusting step to incrementally increase compression over time.

3. The method of claim 1, further comprising placing at least one article of clothing on the user over the belt.

4. The method of claim 1, further comprising ceasing use of the belt when relaxin is no longer present at elevated levels in the user's system.

5. A method for reducing the width of a user's hips, the method comprising the steps of:
    securing a belt around the hips of the user during a time when relaxin is present at elevated levels in the user's system due to recent pregnancy;

applying compression through use of the belt to the user's hips to narrow the user's hips, wherein the applied compression is insufficient to cause immobility of the pelvis of the user;

incrementally adjusting the belt to further compress the user's hips; and ceasing use of the belt when relaxin is no longer present at elevated levels in the user's system.

* * * * *